United States Patent
Libbus et al.

(10) Patent No.: US 7,570,999 B2
(45) Date of Patent: Aug. 4, 2009

(54) IMPLANTABLE DEVICE FOR TREATING EPILEPSY AND CARDIAC RHYTHM DISORDERS

(75) Inventors: Imad Libbus, St. Paul, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 412 days.

(21) Appl. No.: 11/312,178

(22) Filed: Dec. 20, 2005

(65) Prior Publication Data

US 2007/0142871 A1    Jun. 21, 2007

(51) Int. Cl.
*A61N 1/00* (2006.01)

(52) U.S. Cl. .......................................... 607/20
(58) Field of Classification Search ............. 607/2, 607/4, 9, 20, 45
See application file for complete search history.

(56) References Cited

U.S. PATENT DOCUMENTS

| | | | |
|---|---|---|---|
| 4,702,254 A | 10/1987 | Zabara |
| 4,791,931 A | 12/1988 | Slate |
| 4,880,005 A | 11/1989 | Pless et al. |
| 5,014,698 A | 5/1991 | Cohen |
| 5,111,815 A | 5/1992 | Mower |
| 5,199,428 A | 4/1993 | Obel et al. |
| 5,203,326 A | 4/1993 | Collins |
| 5,224,475 A | 7/1993 | Berg et al. |
| 5,318,592 A | 6/1994 | Schaldach |
| 5,330,507 A | 7/1994 | Schwartz |
| 5,334,221 A | 8/1994 | Bardy |
| 5,356,425 A | 10/1994 | Bardy et al. |
| 5,411,531 A | 5/1995 | Hill et al. |

(Continued)

FOREIGN PATENT DOCUMENTS

EP        0547734 A2    6/1993

(Continued)

OTHER PUBLICATIONS

Caparso, Anthony, et al., "System for Neural Control of Respiration", U.S. Appl. No. 11/151,122, filed Jun. 13, 2005, 28 pgs.

(Continued)

*Primary Examiner*—George Manuel
(74) *Attorney, Agent, or Firm*—Schwegman, Lundberg & Woessner, P.A.

(57) ABSTRACT

Various aspects relate to an implantable device. Various device embodiments comprise at least one pulse generator and a controller to communicate with the pulse generator(s). The pulse generator(s) is (are) adapted to deliver a first electrical signal through at least one electrode positioned proximate to a vagus nerve and to deliver a second electrical signal through at least one electrode positioned within or proximate to the heart. The controller includes a module to provide epilepsy therapy that includes delivering the first electrical signal though the at least one electrode proximate to the vagus nerve and a module to provide a cardiac rhythm management (CRM) therapy that includes delivering the second electrical signal through at least one electrode positioned within or proximate to the heart. The CRM therapy includes at least one therapy selected from an antitachycardia therapy and a cardiac resynchronization therapy (CRT). Other aspects and embodiments are provided herein.

28 Claims, 8 Drawing Sheets

U.S. PATENT DOCUMENTS

| | | |
|---|---|---|
| 5,437,285 A | 8/1995 | Verrier et al. |
| 5,522,854 A | 6/1996 | Ideker et al. |
| 5,540,730 A | 7/1996 | Terry, Jr. et al. |
| 5,578,061 A | 11/1996 | Stroetmann et al. |
| 5,658,318 A | 8/1997 | Stroetmann et al. |
| 5,662,689 A | 9/1997 | Elsberry et al. |
| 5,792,187 A | 8/1998 | Adams |
| 5,817,131 A | 10/1998 | Elsberry et al. |
| 5,893,881 A | 4/1999 | Elsberry et al. |
| 5,916,239 A | 6/1999 | Geddes et al. |
| 6,006,134 A | 12/1999 | Hill et al. |
| 6,018,682 A | 1/2000 | Rise |
| 6,073,048 A | 6/2000 | Kieval et al. |
| 6,104,956 A | 8/2000 | Naritoku et al. |
| 6,134,470 A | 10/2000 | Hartlaub |
| 6,205,359 B1 | 3/2001 | Boveja |
| 6,292,695 B1 | 9/2001 | Webster, Jr. et al. |
| 6,337,997 B1 | 1/2002 | Rise |
| 6,341,236 B1 * | 1/2002 | Osorio et al. ................ 607/45 |
| 6,349,233 B1 | 2/2002 | Adams |
| 6,356,788 B2 | 3/2002 | Boveja |
| 6,371,922 B1 | 4/2002 | Baumann et al. |
| 6,438,423 B1 | 8/2002 | Rezai et al. |
| 6,487,446 B1 | 11/2002 | Hill et al. |
| 6,511,500 B1 | 1/2003 | Rahme |
| 6,522,926 B1 | 2/2003 | Kieval et al. |
| 6,587,727 B2 | 7/2003 | Osorio et al. |
| 6,597,954 B1 | 7/2003 | Pless et al. |
| 6,600,954 B2 | 7/2003 | Cohen et al. |
| 6,610,713 B2 | 8/2003 | Tracey |
| 6,622,041 B2 | 9/2003 | Terry, Jr. et al. |
| 6,628,987 B1 | 9/2003 | Hill et al. |
| 6,658,287 B1 | 12/2003 | Litt et al. |
| 6,671,556 B2 | 12/2003 | Osorio et al. |
| 6,684,105 B2 | 1/2004 | Cohen et al. |
| 6,735,471 B2 | 5/2004 | Hill et al. |
| 6,788,975 B1 | 9/2004 | Whitehurst et al. |
| 6,810,285 B2 | 10/2004 | Pless et al. |
| 6,920,357 B2 | 7/2005 | Osorio et al. |
| 6,934,583 B2 | 8/2005 | Weinberg et al. |
| 6,937,896 B1 | 8/2005 | Kroll |
| 6,965,797 B2 | 11/2005 | Pastore et al. |
| 7,158,832 B2 | 1/2007 | Kieval et al. |
| 7,260,431 B2 | 8/2007 | Libbus et al. |
| 7,277,761 B2 | 10/2007 | Shelchuk |
| 2001/0003799 A1 | 6/2001 | Boveja |
| 2001/0016759 A1 | 8/2001 | Kramer et al. |
| 2002/0016344 A1 | 2/2002 | Tracey |
| 2002/0026222 A1 | 2/2002 | Schauerte et al. |
| 2002/0058877 A1 | 5/2002 | Baumann et al. |
| 2002/0072776 A1 | 6/2002 | Osorio et al. |
| 2002/0077670 A1 | 6/2002 | Archer et al. |
| 2002/0082661 A1 | 6/2002 | Plicchi et al. |
| 2002/0107553 A1 | 8/2002 | Hill et al. |
| 2002/0116030 A1 | 8/2002 | Rezai |
| 2002/0143369 A1 | 10/2002 | Hill et al. |
| 2002/0161410 A1 | 10/2002 | Kramer et al. |
| 2002/0165586 A1 | 11/2002 | Hill et al. |
| 2002/0183237 A1 | 12/2002 | Puskas |
| 2002/0188325 A1 | 12/2002 | Hill et al. |
| 2002/0188326 A1 | 12/2002 | Zheng et al. |
| 2002/0198570 A1 | 12/2002 | Puskas |
| 2003/0004549 A1 | 1/2003 | Hill et al. |
| 2003/0023279 A1 | 1/2003 | Spinelli et al. |
| 2003/0040774 A1 | 2/2003 | Terry et al. |
| 2003/0045914 A1 | 3/2003 | Cohen et al. |
| 2003/0060848 A1 | 3/2003 | Keival et al |
| 2003/0060857 A1 | 3/2003 | Perrson et al. |
| 2003/0060858 A1 | 3/2003 | Kieval et al. |
| 2003/0074039 A1 | 4/2003 | Puskas |
| 2003/0078623 A1 | 4/2003 | Weinberg et al. |
| 2003/0078629 A1 | 4/2003 | Chen |
| 2003/0100924 A1 | 5/2003 | Foreman et al. |
| 2003/0105493 A1 | 6/2003 | Salo |
| 2003/0181951 A1 | 9/2003 | Cates |
| 2003/0181958 A1 | 9/2003 | Dobak, III |
| 2003/0195578 A1 | 10/2003 | Perron et al. |
| 2003/0216792 A1 | 11/2003 | Levin et al. |
| 2003/0229380 A1 | 12/2003 | Adams et al. |
| 2003/0236558 A1 | 12/2003 | Whitehurst et al. |
| 2004/0010303 A1 | 1/2004 | Bolea |
| 2004/0015204 A1 | 1/2004 | Whitehurst et al. |
| 2004/0044377 A1 | 3/2004 | Larsson |
| 2004/0138721 A1 | 7/2004 | Osorio et al. |
| 2004/0158295 A1 | 8/2004 | Dyjach et al. |
| 2004/0162594 A1 | 8/2004 | King |
| 2004/0172074 A1 | 9/2004 | Yoshihito |
| 2004/0172075 A1 | 9/2004 | Shafer et al. |
| 2004/0172089 A1 | 9/2004 | Whitehurst et al. |
| 2004/0172094 A1 | 9/2004 | Cohen et al. |
| 2004/0193231 A1 | 9/2004 | David et al. |
| 2004/0215289 A1 | 10/2004 | Fukui |
| 2004/0220621 A1 | 11/2004 | Zhou et al. |
| 2005/0015129 A1 | 1/2005 | Mische |
| 2005/0021092 A1 | 1/2005 | Yun et al. |
| 2005/0065575 A1 | 3/2005 | Dobak |
| 2005/0075701 A1 | 4/2005 | Shafer |
| 2005/0085864 A1 | 4/2005 | Schulman et al. |
| 2005/0096705 A1 | 5/2005 | Pastore et al. |
| 2005/0143779 A1 | 6/2005 | Libbus |
| 2005/0143785 A1 | 6/2005 | Libbus |
| 2005/0143787 A1 | 6/2005 | Boveja et al. |
| 2005/0149126 A1 | 7/2005 | Libbus |
| 2005/0149127 A1 | 7/2005 | Libbus |
| 2005/0149128 A1 | 7/2005 | Heil, Jr. et al. |
| 2005/0149129 A1 | 7/2005 | Libbus et al. |
| 2005/0149130 A1 | 7/2005 | Libbus |
| 2005/0149131 A1 | 7/2005 | Libbus et al. |
| 2005/0149132 A1 | 7/2005 | Libbus |
| 2005/0149133 A1 | 7/2005 | Libbus et al. |
| 2005/0149143 A1 | 7/2005 | Libbus et al. |
| 2005/0149156 A1 | 7/2005 | Libbus et al. |
| 2005/0182288 A1 | 8/2005 | Zabara |
| 2005/0182453 A1 | 8/2005 | Whitehurst et al. |
| 2005/0187584 A1 | 8/2005 | Denker et al. |
| 2005/0197600 A1 | 9/2005 | Schuler et al. |
| 2005/0251216 A1 | 11/2005 | Hill et al. |
| 2005/0261741 A1 | 11/2005 | Libbus et al. |
| 2006/0079945 A1 | 4/2006 | Libbus |
| 2006/0095080 A1 | 5/2006 | Libbus et al. |
| 2006/0106429 A1 | 5/2006 | Libbus et al. |
| 2006/0116737 A1 | 6/2006 | Libbus |
| 2006/0167497 A1 | 7/2006 | Armstrong et al. |
| 2006/0206153 A1 | 9/2006 | Libbus et al. |
| 2006/0206154 A1 | 9/2006 | Moffitt et al. |
| 2006/0206159 A1 | 9/2006 | Moffitt et al. |
| 2006/0217772 A1 | 9/2006 | Libbus et al. |
| 2006/0241699 A1 | 10/2006 | Libbus et al. |
| 2006/0259083 A1 | 11/2006 | Libbus et al. |
| 2007/0021790 A1 | 1/2007 | Kieval et al. |
| 2007/0021799 A1 | 1/2007 | Kieval et al. |
| 2007/0038261 A1 | 2/2007 | Kieval et al. |
| 2007/0142864 A1 | 6/2007 | Libbus et al. |
| 2008/0015648 A1 | 1/2008 | Libbus et al. |
| 2008/0167694 A1 | 7/2008 | Bolea et al. |
| 2008/0200959 A1 | 8/2008 | Libbus et al. |
| 2008/0228238 A1 | 9/2008 | Libbus |

FOREIGN PATENT DOCUMENTS

| | | | |
|---|---|---|---|
| EP | 0688578 | A1 | 12/1995 |
| EP | 0709112 | | 5/1996 |
| EP | 0721786 | A2 | 7/1996 |
| EP | 1304135 | A2 | 4/2003 |

| | | | |
|---|---|---|---|
| EP | 1486232 A2 | 12/2004 | |
| EP | 1541193 A1 | 6/2005 | |
| WO | WO-9216257 A1 | 10/1992 | |
| WO | WO-9713550 A1 | 4/1997 | |
| WO | WO-00/04950 | 2/2000 | |
| WO | WO-0226318 A1 | 4/2002 | |
| WO | WO-0234327 A2 | 5/2002 | |
| WO | WO-02085448 A2 | 10/2002 | |
| WO | WO-02087694 A1 | 11/2002 | |
| WO | WO-3041559 A2 | 5/2003 | |
| WO | WO-03076008 A1 | 9/2003 | |
| WO | WO-03082080 A3 | 10/2003 | |
| WO | WO-03099373 A2 | 12/2003 | |
| WO | WO-03099377 A1 | 12/2003 | |
| WO | WO-2004012814 A1 | 2/2004 | |
| WO | WO-2004084990 A1 | 10/2004 | |
| WO | WO-2004084993 A1 | 10/2004 | |
| WO | WO-2004103455 A2 | 12/2004 | |
| WO | WO-2004105870 A1 | 12/2004 | |
| WO | WO-2004110549 A2 | 12/2004 | |
| WO | WO-2004110550 A2 | 12/2004 | |
| WO | WO-2005018739 A1 | 3/2005 | |
| WO | WO-2005042091 A1 | 5/2005 | |
| WO | WO-2006055436 A1 | 5/2005 | |
| WO | WO-2005063332 A1 | 7/2005 | |
| WO | WO-2005065771 A1 | 7/2005 | |
| WO | WO-2005113066 A1 | 12/2005 | |
| WO | WO-2006031331 A1 | 3/2006 | |
| WO | WO-2006121929 A1 | 11/2006 | |
| WO | WO-2007078410 A1 | 7/2007 | |
| WO | WO-2008063396 A1 | 5/2008 | |

OTHER PUBLICATIONS

Caparso, Anthony, "System for Selective Activation of a Nerve Trunk Using a Transvascular Reshaping Lead", U.S. Appl. No. 11/130,022, filed May 16, 2005, 33 Pgs.

Caparso, Anthony, et al., "Vascularly Stabilized Peripheral Nerve Cup Assembly", U.S. Appl. No. 11/151,103, filed Jun. 13, 2005, 41 pgs.

Cyberonics, "NeuroCybernetic Prosthesis System NCPA Pulse Generator Models 100 and 101", *Physician's Manual*, (Aug. 2002), 1-152.

Holder, L. K., "Treatment of refactory partial seizures: preliminary results of a controlled study", *Pacing & Clinical Electrophysiology*, 15(10 Pt 2), (Oct. 1992), 1557-71.

Libbus, Imad, "Cardiac Rhythm Management Device With Neural Sensor", U.S. Appl. No. 10/992,320, filed Nov. 18, 2004, 65 pgs.

Libbus, Imad, et al., "Cell Therapy and Neural Stimulation for Cardiac Repair", U.S. Appl. No. 11/063,170, filed Feb. 22, 2005, 42 pgs.

Libbus, Imad, et al., "Implantable Neural Stimulator With Mode Switching", U.S. Appl. No. 11/137,038, filed May 25, 2005, 42 pgs.

Libbus, I., "Integrated Lead for Applying Cardiac Resynchronization Therapy and Neural Stimulation Therapy", U.S. Appl. No. 11/077,970, filed Mar. 11, 2005, 67 pgs.

Libbus, Imad, et al., "Method and Apparatus for Controlling Autonomic Balance Using Neural Stimulation", U.S. Appl. No. 11/124,791, filed May 9, 2005, 47 pgs.

Libbus, Imad, "Method and Apparatus for Simultaneously Presenting Cardiac and Neural Signals", U.S. Appl. No. 11/114,246, filed Apr. 25, 2005, 58 Pgs.

Libbus, I., et al., "Method and Apparatus for Synchronizing Neural Simulation to Cardiac Cycles", U.S. Appl. No. 11/099,141, filed Apr. 5, 2005.

Libbus, Imad, et al., "Neural Stimulation System to Prevent Simultaneous Energy Discharges", U.S. Appl. No. 11/110,542, filed Apr. 20, 2005, 36 pgs.

Libbus, Imad, "Neural Stimulation With Avoidance of Inappropriate Stiumlation", U.S. Appl. No. 11/000,249, filed Nov. 30, 2004, 45 pgs.

Libbus, Imad, et al., "Safety Control System for Implantable Neural Stimulator", U.S. Appl. No. 11/135,883, filed May 24, 2005, 43 pgs.

Libbus, Imad, "Stimulator for Auricular Branch of Vagus Nerve", U.S. Appl. No. 11/005,703, filed Dec. 7, 2004, 35 pgs.

Libbus, I., et al., "System and Method for Closed-Loop Neural Stimulation", U.S. Appl. No. 10/992,319, filed Nov. 18, 2004.

Libbus, Imad, et al., "System and Method for Filtering Neural Stimulation", U.S. Appl. No. 10/982,001, filed Nov. 4, 2004, 59 pgs.

Libbus, Imad, "System and Method to Deliver Therapy in Presence of Another Therapy", U.S. Appl. No. 11/125,503, filed May 10, 2005, 39 pgs.

Libbus, Imad, "System to Provide Myocardial and Neural Stimulation", U.S. Appl. No. 11/087,935, filed Mar. 23, 2005, 52 pgs.

Libbus, Imad, et al., "System to Provide Neural Markers for Sensed Neural Activity", U.S. Appl. No. 11/113,773, filed Apr. 25, 2005, 52 pgs.

Moffitt, Julia, "Combined Neural Stimulation and Cardiac Resynchronization Therapy", U.S. Appl. No. 11/078,460, filed Mar. 11, 2005, 35 pgs.

Moffitt, Julia, et al., "Neural Stimulator System for Cardiac Fat Pads", U.S. Appl. No. 11/077,583, filed Mar. 11, 2005, 37 pgs.

Moffitt, Julia, et al., "System to Treat AV-Conducted Ventricular Tachyarrhythmia", U.S. Appl. No. 11/099,226, filed Apr. 5, 2005, 39 pgs.

Moffitt, Julia, et al., "Transvascular Neural Stimulation Device", U.S. Appl. No. 11/103,245, filed Apr. 11, 2005, 33 pgs.

Thompson, Gregory W., "Bradycardia induced by intravascular versus direct stimulation of the vagus nerve", *Annals of Thoracic Surgery*, 65(3), (Mar. 1998), 637-642.

"International Search Report and Written Opinion for Application No. PCT/US2006/042727", (Apr. 23, 2007), 16.

McGregor, A., et al., "Right-Sided Vagus Nerve Stimulation as a Treatment for Refractory Epilepsy in Humans", *Epilepsia*; 46(1), (Jan. 2005),91-96.

Rugg-Gunn, F. J, et al., "Cardiac arrhythmias in focal epilepsy: a prospective long-term study.", *Lancet*, 364(9452), (Dec. 18-31, 2004), 2212-9.

06827323.4, "European Application Serial No. 06827323.4, Office Action mailed Nov. 12, 2008.", 3 pgs.

* cited by examiner

IMPLANTABLE DEVICE FOR TREATING EPILEPSY AND CARDIAC RHYTHM DISORDERS

RELATED APPLICATIONS

This patent application is related to the following co-pending and commonly assigned U.S. Patent Applications, the disclosures of which are herein incorporated by reference in their entirety: "Multi-Site Ventricular Pacing Therapy With Parasympathetic Stimulation," Ser. No. 10/700,368, filed Nov. 3, 2003; "Lead for Stimulating the Baroreceptors in the Pulmonary Artery," Ser. No. 10/746,861, filed Dec. 24, 2003; "Combined Remodeling Control Therapy and Anti-Remodeling Therapy By Implantable Cardiac Device," Ser. No. 10/850,341, filed May 20, 2004; "Integrated Lead for Applying Cardiac Resynchronization Therapy and Neural Stimulation Therapy," Ser. No. 11/077,970, filed Mar. 11, 2005; "System to Provide Myocardial and Neural Stimulation," Ser. No. 11/087,935, filed Mar. 23, 2005, "Automatic Baroreflex Modulation Based on Cardiac Activity," US Publication 20050149132; "Automatic Baroreflex Modulation Responsive To Adverse Event," US Publication 20050149127; "Baropacing and Cardiac Pacing to Control Output," US Publication 20050149129; "System and Method for Filtering Neural Stimulation," Ser. No. 10/982,001, filed Nov. 4, 2004; "Neural Stimulation With Avoidance of Inappropriate Stimulation," Ser. No. 11/000,249, filed Nov. 30, 2004; "System and Method to Deliver Therapy in Presence of Another Therapy," Ser. No. 11/125,503, filed May 10, 2005; "Neural Stimulation System to Prevent Simultaneous Energy Discharges," Ser. No. 11/110,542, filed Apr. 20, 2005.

TECHNICAL FIELD

This application relates generally to medical devices and, more particularly, to implantable devices capable of providing therapy for epilepsy and cardiac rhythm disorders.

BACKGROUND

Vagal nerve stimulation (VNS) is an FDA-approved therapy in reducing the frequency of seizures that are refractory to antiepileptic medication. Clinical studies have concluded that VNS therapy is both safe and effective in controlling seizures. Cyberonics, Inc. of Houston, Tex. has manufactured a VNS device that has been marketed.

SUMMARY

Various aspects of the present subject matter relate to an implantable device. Various device embodiments comprise at least one pulse generator and a controller adapted to communicate with the pulse generator(s). The pulse generator(s) is (are) adapted to deliver a first electrical signal through at least one electrode positioned proximate to a vagus nerve and to deliver a second electrical signal through at least one electrode positioned within or proximate to the heart. The controller includes a module to provide epilepsy therapy that includes delivering the first electrical signal though the at least one electrode proximate to the vagus nerve and a module to provide a cardiac rhythm management (CRM) therapy that includes delivering the second electrical signal through at least one electrode positioned within or proximate to the heart. The CRM therapy includes at least one therapy selected from an antitachycardia therapy and a cardiac resynchronization therapy (CRT). For example, some embodiments provide an antitachycardia therapy without a CRM therapy, some embodiments provide a CRM therapy without an antitachycardia therapy, and some embodiments provide both a CRM therapy and an antitachycardia therapy.

Various aspects of the present subject matter relate to a method of operating an implantable device. According to various embodiments of the method, epilepsy therapy is provided, including using the implantable device to deliver an electrical stimulation to a vagus nerve; and a cardiac rhythm management (CRM) therapy is provided. The CRM therapy includes at least one therapy selected from an antitachycardia therapy and a cardiac resynchronization therapy (CRT). Providing the CRM therapy includes using the implantable device to deliver an electrical stimulation to capture myocardial tissue.

This Summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their equivalents.

DETAILED DESCRIPTION

Figure 1A:
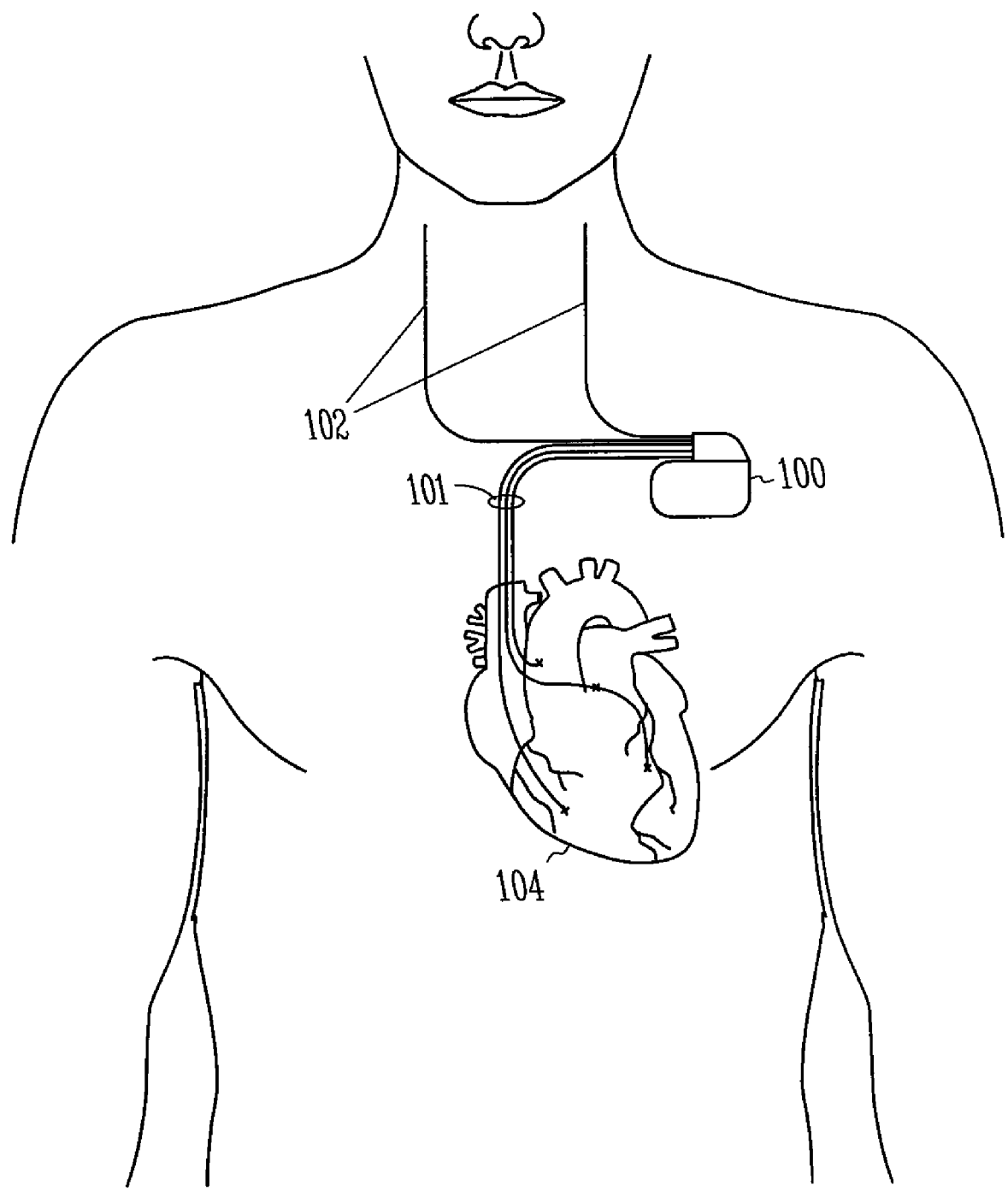
FIGS. 1A-1B illustrate some device embodiments that provide epilepsy and CRM therapy.

Patients with epileptic seizures commonly experience cardiac rhythm disorders, such as tachycardia, fibrillation, bradycardia, and asystole. The present subject matter provides an implantable device adapted to provide vagal nerve stimulation to treat epilepsy, and to provide cardiac rhythm management (CRM) therapy. Such an implantable device is capable for use in a patient who is indicated for an anti-epilepsy VNS and who is also indicated for a CRM device, such as a pacemaker or defibrillator. According to various embodiments, the CRM therapy includes electrical antitachycardia therapy. Electrical antitachycardia therapy includes antitachycardia pacing and antitachycardia defibrillation shocks. Some device embodiments are adapted to simultaneously provide epilepsy therapy and CRM therapy. According to various embodiments, the CRM therapy includes cardiac resynchronization therapy (CRT). Some embodiments provide combinations of two or more CRM therapies, such as cardiac pacing and antitachycardia therapy, cardiac pacing and CRT, cardiac antitachycardia therapy and CRT, and cardiac pacing, cardiac antitachycardia therapy and CRT. For example, various embodiments provide a device to simultaneously provide anti-epileptic VNS therapy as well as CRM therapy, such as bradycardia pacing and antitachycardia therapy.

Some embodiments use an intravascularly lead in the internal jugular vein positioned proximate to a vagus nerve to transvascularly stimulate the vagus nerve using at least one electrode in the internal jugular vein. Some embodiments use an intravascularly lead in a vessel other than the internal jugular vein that passes proximate to the vagus nerve. For example, a lead can be fed into the azygous vein to position at least one electrode functionally proximate to a vagus nerve to provide therapeutic stimulation to the vagus nerve. Some embodiments use a lead with nerve cuff electrode adapted to stimulate the vagus nerve. Various embodiments provide at least one lead to stimulate the left vagus nerve, various embodiments provide at least one lead to stimulate the right vagus nerve, and various embodiments provide at least one lead to stimulate the left vagus nerve and at least one lead to stimulate the right vagus nerve.

One example of a CRM lead is an intravascularly-fed lead fed into or proximate to the heart to provide single-chamber pacing, dual-pacing, and/or antitachycardia therapies. Some embodiments use epicardial leads to provide the CRM therapy. The following disclosure addresses electrical stimulation for epilepsy and electrical stimulation for CRM therapy, including pacing/antitachycardia therapies and CRT therapies.

Various embodiments treat both epilepsy and cardiac rhythm disorders using one device; and various embodiments use more than one device adapted to communicate with each other to treat epilepsy and cardiac rhythm disorders. Communication between devices can be through a wire connecting the devices, or can use wireless technology such as radio frequency or ultrasound technology. Thus, the delivery of the therapies can be integrated, allowing more appropriate therapy to be delivered because of knowledge of the other therapy than if neither therapy accounted for the other therapy. Examples of such integration are provided below. Vagal stimulation can be modulated based on cardiac activity (see, for example, "Automatic Baroreflex Modulation Based on Cardiac Activity," U.S. Publication 20050149132, which has been incorporated by reference). Thus, heart rhythms and heart rate can provide feedback for the vagal stimulation. Vagal stimulation can be modulated in response to an adverse event to, for example, reduce myocardial ischemic damage when a myocardial infarction is detected (see, for example, "Automatic Baroreflex Modulation Responsive To Adverse Event," U.S. Publication 20050149127, which has been incorporated by reference). Cardiac pacing can compensate for any compromise of cardiac output caused by the vagal stimulation (see, for example, "Baropacing and Cardiac Pacing to Control Output," U.S. Publication 20050149129, which has been incorporated by reference). CRM sensing can appropriately filter or otherwise compensate for neural stimulation artifacts (see, for example, "System and Method for Filtering Neural Stimulation," Ser. No. 10/982,001, filed Nov. 4, 2004, which has been incorporated by reference). Neural stimulation of the vagus can avoid unintentional stimulation of myocardial tissue or unintentional stimulation of other neural paths, such as neural paths that affect heart rhythm (see, for example, "Neural Stimulation With Avoidance of Inappropriate Stimulation," Ser. No. 11/000,249, filed Nov. 30, 2004, which has been incorporated by reference). The therapies can compensate for each other by using different parameter sets, depending on, for example, whether the other therapy is present (see, for example, "System and Method to Deliver Therapy in Presence of Another Therapy," Ser. No. 11/125,503, filed May 10, 2005, which has been incorporated by reference). The electrical therapies can be delivered in such a manner as to avoid undesired interactions between neural stimulation electrodes and CRM electrodes (see, for example, "Neural Stimulation System to Prevent Simultaneous Energy Discharges," Ser. No. 11/110,542, filed Apr. 20, 2005, which has been incorporated by reference).

EPILEPSY TREATMENT

A number of drugs are approved to treat epilepsy. However, not all patients respond well to drug treatment. Brain surgery also has been used as epilepsy treatment. However, surgery can involve complications, such as unintended brain damage, and often is not fully successful.

Electrical stimulation is an emerging therapy for controlling or preventing epilepsy, and has been indicated for use to reduce the frequency of seizures in some patients who are refractory to antiepileptic medications. For example, one epilepsy treatment that stimulates the vagus nerve is described in U.S. Pat. No. 4,702,254 entitled "Neurocybernetic Prosthesis." The device identified in the patent includes a pulse generator which generates electrical pulses having a frequency of between 30 and 300 cycles per second, and a pulse duration of between 0.3 and 1 millisecond and a constant current of between 1 and 20 milliamperes. The electrical signal from the generator is varied after it has been implanted to "tune" the electrical signal to the patient. The device could be turned on automatically in response to sensed wave activity, or manually when the patient senses that a convulsion is imminent. U.S. Pat. No. 4,702,254 is herein incorporated by reference in its entirety.

Cyberonics, Inc. has manufactured a vagal nerve stimulation (VNS) therapy device, which has been marketed for epilepsy therapy. The VNS device uses a bipolar lead to stimulate the vagus nerve. Vagal nerve stimulation for epilepsy therapy can use an electrical stimulation signal with an output current of 0 to approximately 3.5 mA, a frequency within a range of approximately 1 to 30 Hz, a pulse width within a range of approximately 130 to 1000 μsec, and stimulation pulses of with an "on time" within a range of 7 to 270 seconds and an "off time" within a range of 0.2 to and 180 minutes. The duty cycles in this device can range from approximately 2% to 97%. The stimulation therapy can be programmed. The IMD of the present subject matter is capable of providing such electrical stimulation to a vagus nerve (including the left vagus nerve, the right vagus nerve, and both the left and right vagus nerves) to provide the desired therapy for epilepsy.

The programmed vagal stimulation therapy repeats the stimulation according to the programmed on and off time. The patient can also initiate a therapy. A magnet can be used. Other wireless communication methods can be used for the patient-initiated therapy, including RF communication, ultrasound communication, and inductive communication.

CARDIAC RHYTHM TREATMENT

Pacing/Antitachycardia Therapies When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias uses a cardiac rhythm management (CRM) system. Such systems are often implanted in the patient and deliver therapy to the heart.

CRM systems include, among other things, pacemakers. Pacemakers deliver timed sequences of low energy electrical stimuli, called pace pulses, to the heart, such as via an intravascular leadwire or catheter (referred to as a "lead") having one or more electrodes disposed in or about the heart. Heart contractions are initiated in response to such pace pulses. By properly timing the delivery of pace pulses, the heart can be induced to contract in proper rhythm, greatly improving its efficiency as a pump. Pacemakers are often used to treat patients with bradyarrhythmias, that is, hearts that beat too slowly, or irregularly.

A variety of cardiac pacemakers are known and commercially available. Pacemakers are generally characterized by a number of different aspects of their construction or use, such as which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. Some pacemakers sense electrical cardiac activity in one or more of the chambers of the heart, and inhibit or trigger delivery of pacing stimuli to the heart based on the occurrence and recognition of sensed intrinsic electrical events. One such pacemaker, for example, senses electrical cardiac activity in the ventricle of the patient's heart, and delivers pacing stimuli to the ventricle only in the absence of electrical signals indicative of natural ventricular contractions. Another type of pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by the second type of pacemaker is timed using prior sensed or paced events.

Pacemakers are also known which respond to other types of physiologically-based signals, such as signals from sensors for measuring the pressure inside the patient's ventricle or for measuring the level of the patient's physical activity. In some rate-responsive pacemakers, the pacing rate is determined according to the output from an activity sensor. The pacing rate is variable between a predetermined maximum and minimum level, which may be selectable from among a plurality of programmable upper and lower rate limit settings. When the activity sensor output indicates that the patient's activity level has increased, the pacing rate is increased from the programmed lower rate by an incremental amount which is determined as a function of the output of the activity sensor.

Cardiac rhythm management systems also include antitachycardia devices. Defibrillators are capable of delivering higher energy electrical stimuli to the heart. Such defibrillators also include cardioverters, which synchronize the delivery of such stimuli to portions of sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. Some antitachycardia devices deliver a train of pacing pulses to an appropriate region of the heart to provide atrial antitachycardia pacing or ventricular antitachycardia pacing. A tachyarrhythmia can be detected. If the tachyarrhythmia is determined to be a fibrillation, a defibrillation shock can be provided. Some detected tachyarrhythmias can be successfully treated with burst pacing at a high frequency without tracking. Some CRM systems combine the functions of pacemakers and antitachycardia devices, drug delivery devices, and any other implantable or external systems or devices for diagnosing or treating cardiac arrhythmias.

CRT

Following myocardial infarction (MI) or other cause of decreased cardiac output, a complex remodeling process of the ventricles occurs that involves structural, biochemical, neurohormonal, and electrophysiologic factors. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation.

As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) accounts for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

The heart pumps more effectively when the chambers contract in a coordinated manner, a result normally provided by the specialized conduction pathways in both the atria and the ventricles that enable the rapid conduction of excitation (i.e., depolarization) throughout the myocardium. These pathways conduct excitatory impulses from the sino-atrial node to the atrial myocardium, to the atrio-ventricular node, and thence to the ventricular myocardium to result in a coordinated contraction of both atria and both ventricles. This both synchronizes the contractions of the muscle fibers of each chamber and synchronizes the contraction of each atrium or ventricle with the contralateral atrium or ventricle. Without the synchronization afforded by the normally functioning specialized conduction pathways, the heart's pumping efficiency is greatly diminished. Pathology of these conduction pathways and other inter-ventricular or intra-ventricular conduction deficits can be a causative factor in heart failure, which refers to a clinical syndrome in which an abnormality of cardiac function causes cardiac output to fall below a level adequate to meet the metabolic demand of peripheral tissues. In order to treat these problems, implantable cardiac devices have been developed that provide appropriately timed electrical stimulation to one or more heart chambers in an attempt to improve the coordination of atrial and/or ventricular contractions, termed cardiac resynchronization therapy (CRT). Ventricular resynchronization is useful in treating heart failure because, although not directly inotropic, resynchronization can result in a more coordinated contraction of the ventricles with improved pumping efficiency and increased cardiac output. Currently, a common form of CRT applies stimulation pulses to both ventricles, either simultaneously or separated by a specified biventricular offset interval, and after a specified atrio-ventricular delay interval with respect to the detection of an intrinsic atrial contraction or delivery of an atrial pace.

Clinical data has shown that cardiac resynchronization therapy (CRT), achieved through synchronized biventricular pacing, results in a significant improvement in cardiac function. It has also been reported CRT can be beneficial in preventing and/or reversing the ventricular remodeling that often occurs in post-MI and heart failure patients. An embodiment of the present subject matter relates to an implantable cardiac device capable of providing remodeling control therapy (RCT) by controlling ventricular activation with cardiac resynchronization pacing of the myocardium.

As provided above, neural stimulation is applied to the vagus nerve with appropriate parameters to provide an epilepsy therapy. Neural stimulation can also be applied as part of CRT.

Neural stimulation has been the subject of a number of studies and has been proposed for several therapies. Direct electrical stimulation of parasympathetic nerves can activate the baroreflex, inducing a reduction of sympathetic nerve activity and reducing blood pressure by decreasing vascular resistance. Sympathetic inhibition, as well as parasympathetic activation, has been associated with reduced arrhythmia vulnerability following a myocardial infarction, presumably by increasing collateral perfusion of the acutely ischemic myocardium and decreasing myocardial damage. Modulation of the sympathetic and parasympathetic nervous system with neural stimulation has been shown to have positive clinical benefits, such as protecting the myocardium from further remodeling and predisposition to fatal arrhythmias following a myocardial infarction. Thus, some embodiments that provide CRT includes anti-remodeling therapy (ART) by stimulating the baroreflex in order to inhibit sympathetic activity to provide a greater therapeutic benefit than either RCT or ART individually. The device controls ventricular activation through synchronized pacing of the right and left ventricles. In addition, the device may provide a combination of parasympathetic stimulation and sympathetic inhibition. Parasympathetic stimulation can be achieved by stimulation of the vagus nerve, while sympathetic inhibition can be achieved through baroreflex stimulation such as stimulation of the aortic or carotid sinus nerve, or stimulation of baroreceptors in the pulmonary artery, for example. The device controls the delivery of RCT and ART independently in either an open-loop or closed-loop fashion, the latter based upon a cardiac function assessment performed by the device.

In various embodiments, the device delivers ART using a lead adapted to be intravascularly disposed to stimulate an appropriate nerve, e.g., near a baroreceptor in the case of sympathetic inhibition or near a parasympathetic nerve, such as the right or left vagus, in the case of parasympathetic stimulation. Some CRT devices include an atrial lead to pace and/or sense the right atrium, a right ventricle lead to pace and/or sense the right ventricle, and a left ventricle lead fed through the coronary sinus to a position to pace and/or sense the left ventricle. A lead within the coronary sinus is capable of being used to transvascularly stimulate target parasympathetic nerves anatomically located on the extravascular surface of the coronary sinus at a strength sufficient to elicit depolarization of adjacent nerves, and is also capable of being used to deliver cardiac resynchronization therapy with appropriately timed pacing pulses at a site proximate to the left ventricle, for example.

According to various embodiments, the device is designed to sense a refractory period, and to deliver the neural stimulation from an electrode or electrodes within the coronary sinus during the refractory period to avoid unintentionally capturing cardiac tissue and inducing an arrhythmia such as atrial fibrillation.

Depending on the intravascular location of the neural stimulation electrode(s), the right vagal branch, the left vagal branch or a combination of the right and left vagal branches are capable of being stimulated. The left and right vagal branches innervate different areas of the heart, and thus provide different results when stimulated. According to present knowledge, the right vagus nerve appears to innervate the right side of the heart, including the right atrium and right ventricle, and the left vagus nerve appears to innervate the left side of the heart, including the left atrium and left ventricle. Stimulation of the right vagus has more chronotropic effects because the sinus node is on the right side of the heart. Thus, various embodiments selectively stimulate the right vagus nerve and/or the left vagus nerve to selectively control contractility, excitability, and inflammatory response on the right and/or left side of the heart. Since the venous system is for the most part symmetrical, leads can be fed into an appropriate vessel to transvascularly stimulate the right or left vagus nerve. For example, a lead in the right internal jugular vein can be used to stimulate the right vagus nerve and a lead in the left internal jugular vein can be used to stimulate the left vagus nerve. Some embodiments use nerve cuffs to stimulate the target nerve, and some embodiments use a wireless link between the implantable medical device (IMD) and the electrodes to stimulate the neural target.

DEVICE EMBODIMENTS

Figure 1B:
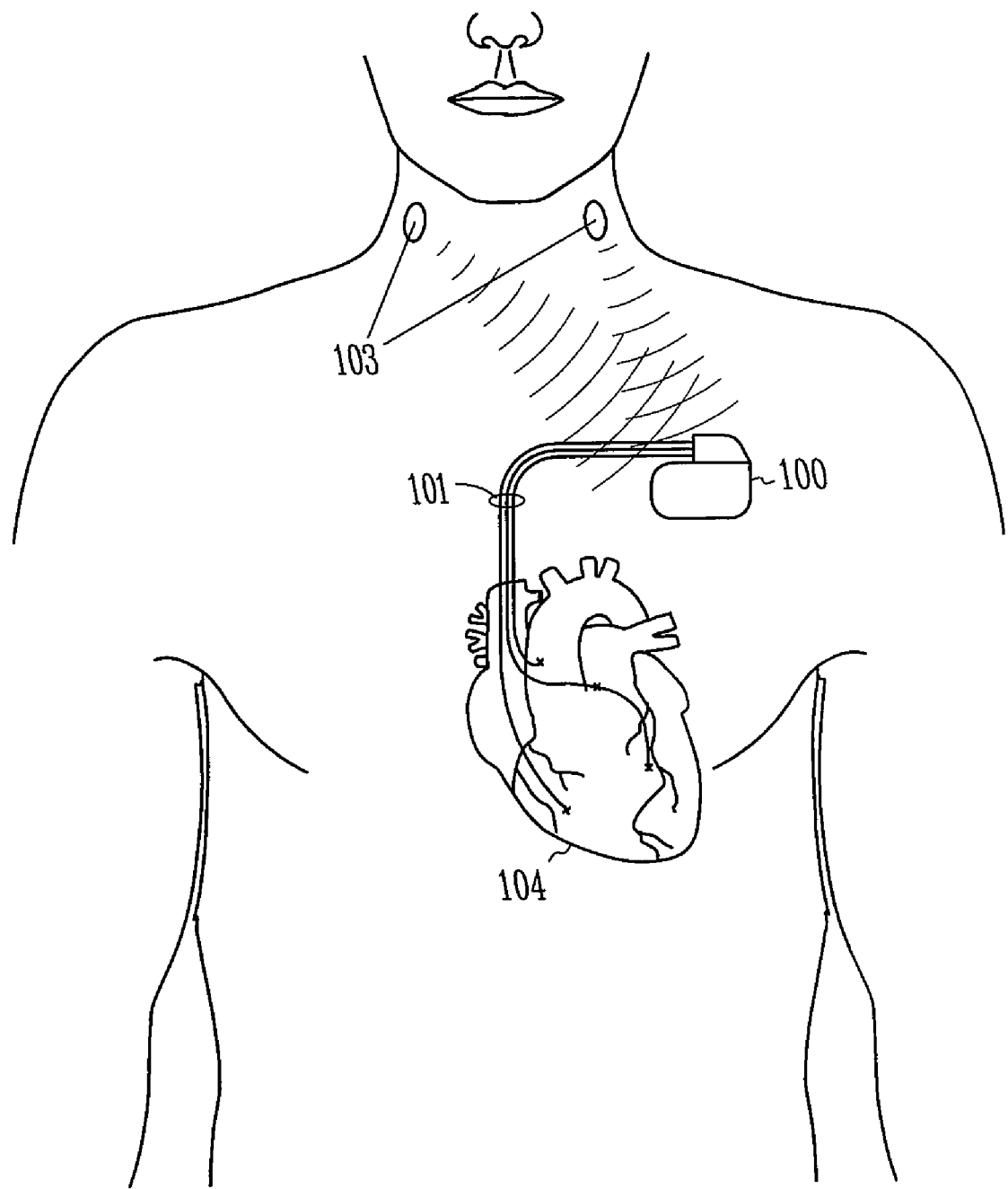

FIGS. 1A-1B illustrate some device embodiments that provide epilepsy and CRM therapy. FIG. 1A illustrates an implantable medical device (IMD) 100 placed subcutaneously or submuscularly in a patient's chest with lead(s) 101 positioned to provide a CRM therapy to a heart 104, and with lead(s) 102 positioned to stimulate at least one vagus nerve as part of an epilepsy therapy. According to various embodiments, the leads are positioned in or proximate to the heart to provide a desired cardiac pacing therapy. In some embodiments, the lead(s) are positioned in or proximate to the heart to provide a desired defibrillation therapy. In some embodiments, the lead(s) are positioned in or proximate to the heart to provide a desired CRT therapy. Some embodiments place the leads in positions with respect to the heart that enable the lead(s) to deliver the combinations of at least two of the pacing, defibrillation and CRT therapies. According to various embodiments, vagus nerve stimulation lead(s) are used to stimulate the left vagus nerve, to stimulate the right vagus nerve, or to stimulate both the left and right vagus nerves.

Some vagus. nerve stimulation lead embodiments are subcutaneously tunneled to a vagus nerve, and can have a nerve cuff electrode to stimulate the vagus nerve. Some vagus nerve stimulation lead embodiments are intravascularly fed into a vessel proximate to vagus nerve, and use electrode(s) within the vessel to transvascularly stimulate the vagus nerve. For example, some embodiments stimulate the vagus using electrode(s) positioned within the internal jugular vein and/or within the azygous vein.

FIG. 1B illustrates an implantable medical device (IMD) 100 with lead(s) 101 positioned to provide a CRM therapy to a heart 104, and with satellite electrode(s) 103 positioned to stimulate at least one vagus nerve as part of an epilepsy therapy. The satellite electrode(s) are connected to the IMD, which functions as the planet for the satellites, via a wireless link. Stimulation and communication can be performed through the wireless link. Examples of wireless links include RF links and ultrasound links. Although not illustrated, some embodiments perform myocardial stimulation using wireless links.

Figure 2A:
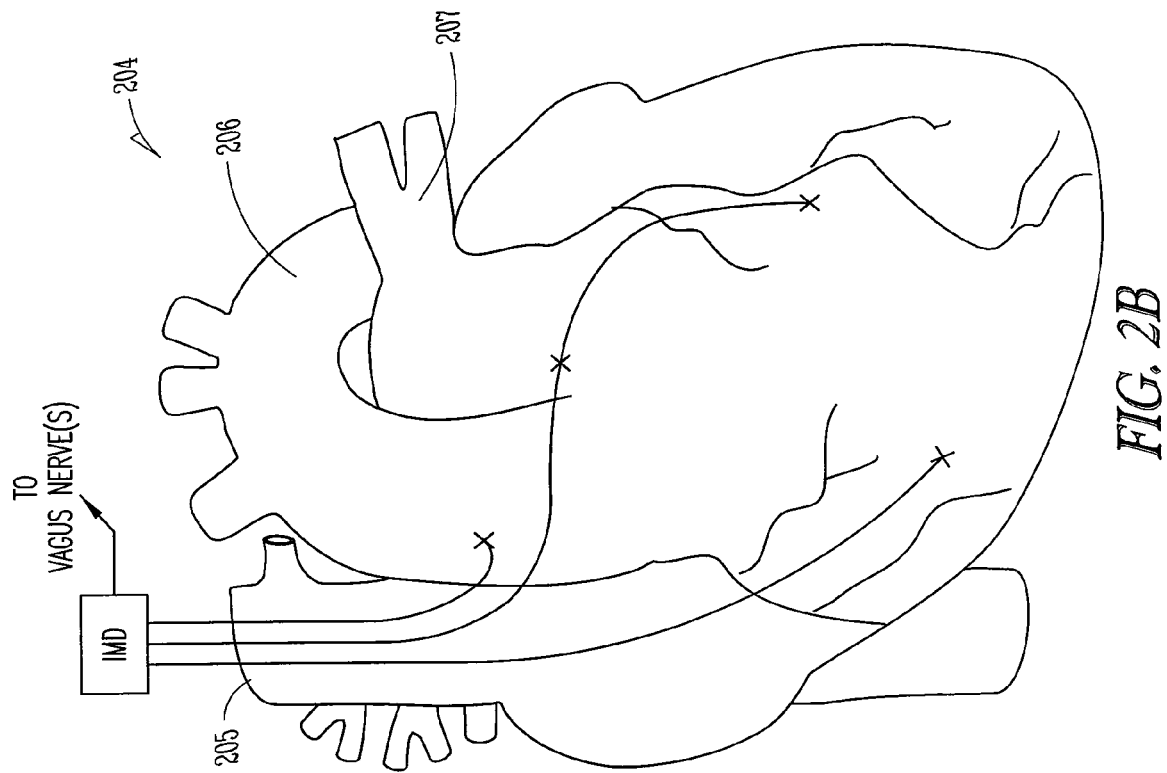
FIGS. 2A-2D illustrate a heart, and is useful for describing stimulation positions.
Figure 2B:
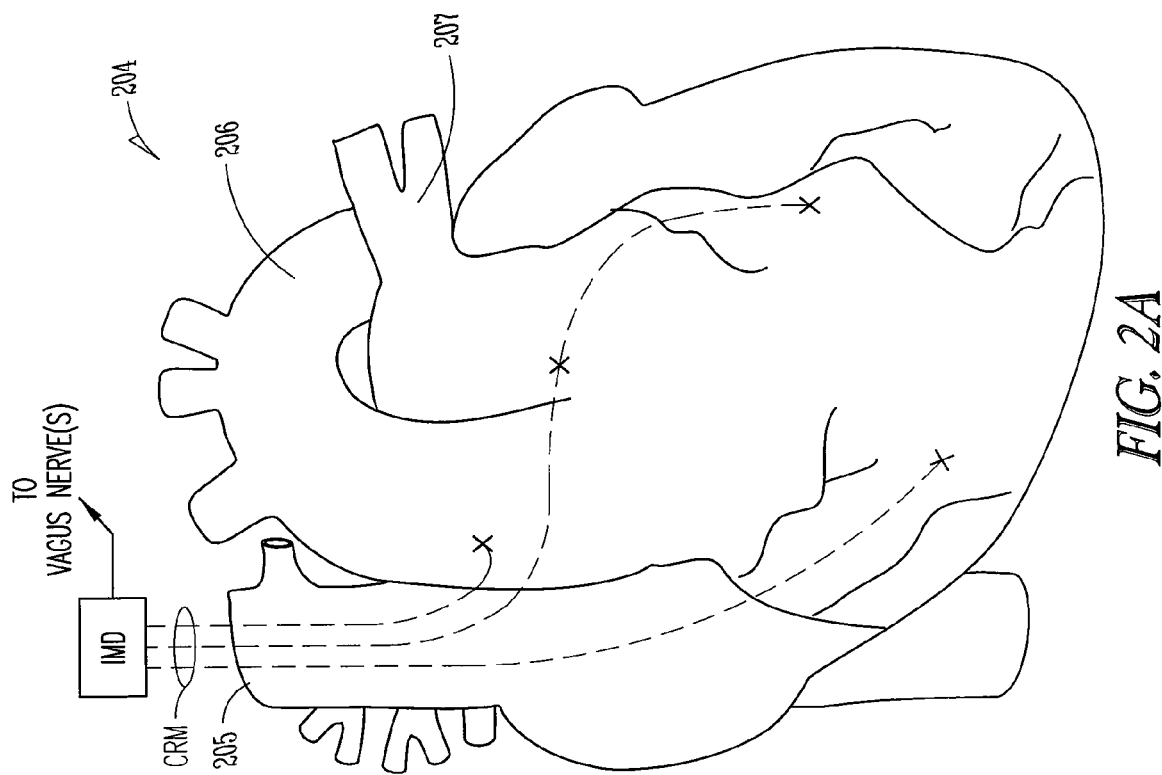
Figure 2D:
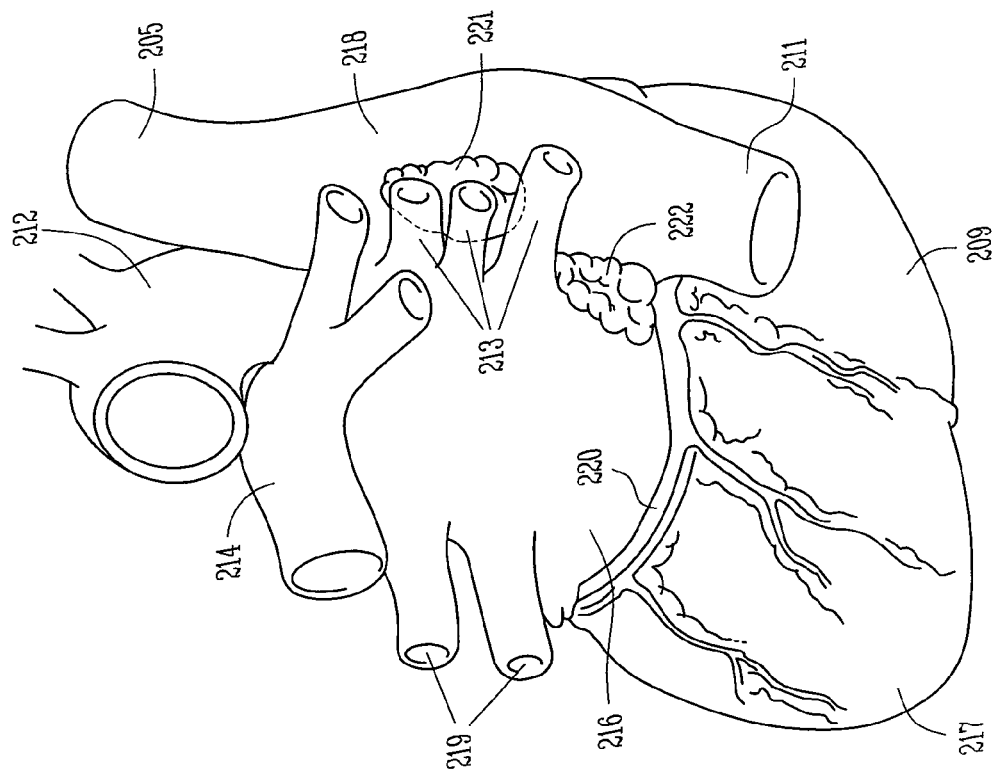
Figure 2C:
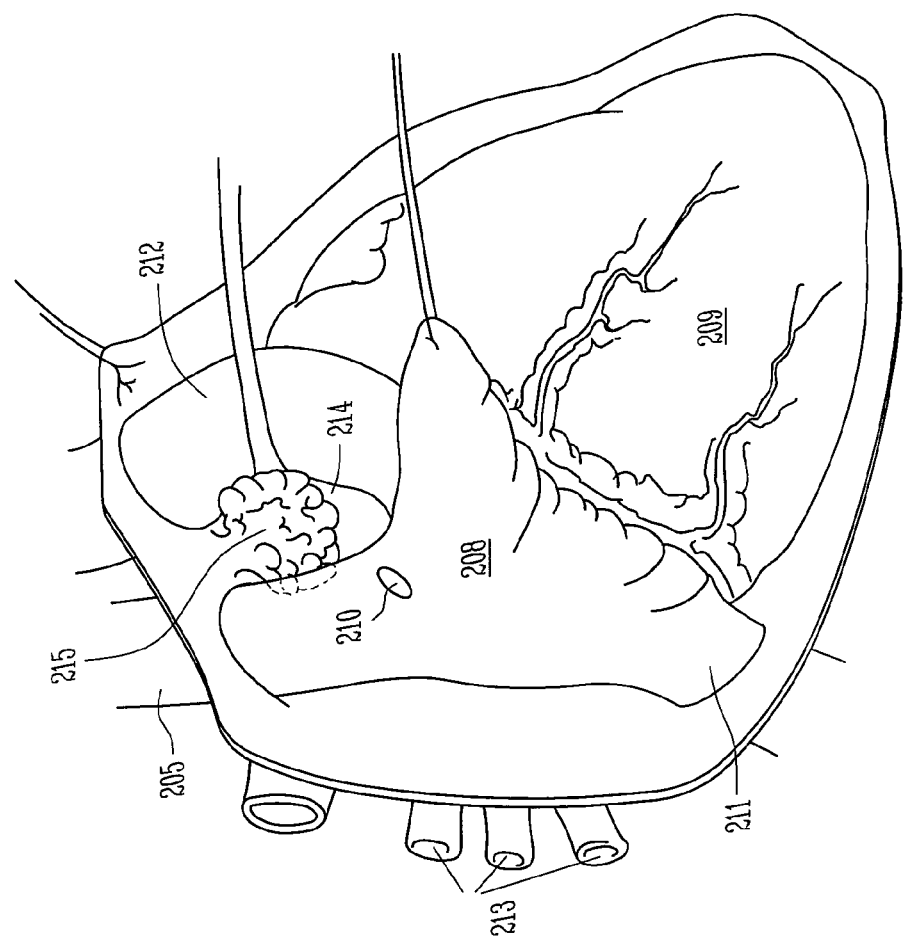

FIGS. 2A-2D illustrate a heart, and is useful for describing stimulation positions. As illustrated in FIGS. 2A-2B, the heart 204 includes a superior vena cava 205, an aortic arch 206, and a pulmonary artery 207. CRM leads pass nerve sites that can be stimulated to provide ART as part of cardiac resynchronization therapy (CRT). For example, CRM leads are capable of being intravascularly inserted through a peripheral vein and into the coronary sinus, and are capable of being intravascularly inserted through a peripheral vein and through the tricuspid valve into the right ventricle of the heart (not expressly shown in the figure) similar to a cardiac pacemaker lead, and continue from the right ventricle through the pulmonary valve into the pulmonary artery. The coronary sinus and pulmonary artery are provided as examples of vasculature proximate to the heart in which a lead can be intravascularly inserted to stimulate nerves within or proximate to the vasculature. Thus, according to various aspects of the present subject matter, parasympathetic nerves are stimulated in or around vasculature located proximate to the heart by at least one electrode intravascularly inserted therein. Alternatively, a wireless stimulating device may be positioned via catheter into the vasculature located proximate to the heart. Control of stimulation and/or energy for stimulation may be supplied by another implantable or external device via ultrasonic, electromagnetic or a combination thereof. FIGS. 2C and 2D illustrate the right side and left side of the heart, respectively, and further illustrate cardiac fat pads which have nerve endings that function as baroreceptor sites. FIG. 2C illustrates the right atrium 208, right ventricle 209, sinoatrial node 210, superior vena cava 205, inferior vena cava 211, aorta 212, right pulmonary veins 213, and right pulmonary artery 214. FIG. 2C also illustrates a cardiac fat pad 215 between the superior vena cava and aorta. Nerve endings in the cardiac fat pad 215 are stimulated in some embodiments using an electrode screwed into or otherwise placed in the fat pad, and are stimulated in some embodiments using an intravenously-fed lead proximately positioned to the fat pad in a vessel such as the right pulmonary artery or superior vena cava, for example. FIG. 2D illustrates the left atrium 216, left ventricle 217, right atrium 218, right ventricle 209, superior vena cava 205, inferior vena cava 211, aorta 212, right pulmonary veins 213, left pulmonary veins 219, right pulmonary artery 214, and coronary sinus 220. FIG. 2D also illustrates a cardiac fat pad 221 located proximate to the right cardiac veins and a cardiac fat pad 222 located proximate to the inferior vena cava and left atrium. Nerve endings in the fat pad 221 are stimulated in some embodiments using an electrode screwed into the fat pad 221, and are stimulated in some embodiments using an intravenously-fed lead proximately positioned to the fat pad in a vessel such as the right pulmonary artery 214 or right pulmonary veins 213, for example. Nerve endings in the fat pad 222 are stimulated in some embodiments using an electrode screwed into the fat pad, and are stimulated in some embodiments using an intravenously-fed lead proximately positioned to the fat pad in a vessel such as the inferior vena cava 211 or coronary sinus or a lead in the left atrium 216, for example.

FIG. 2A also illustrates an implantable medical device with CRM lead(s) to perform CRM therapy and with neural stimulation (NS) lead(s) to perform epilepsy therapy. The CRM leads illustrated in FIG. 2A are represented by the dotted lines and electrodes are represented by "X." The illustrated CRM leads are fed into the right atrium, right ventricle, and coronary sinus of the heart. FIG. 2B also illustrates an implantable medical device with CRM lead(s) to perform CRM therapy and with neural stimulation (NS) lead(s) to perform epilepsy therapy. The CRM leads illustrated in FIG. 2B are represented by the solid lines and electrodes represented by "X" epicardially positioned proximate to the heart to perform the CRM therapy.

With respect to FIGS. 2A and 2B, the CRM leads can also provide selective neural stimulation, such as may be performed to provide ART as part of a CRT therapy. Some embodiments provide the neural stimulation and the mycardial stimulation using integrated NS/myocardial stimulation leads, and some embodiments use NS leads and separate myocardial stimulation leads. In the embodiments illustrated in FIGS. 2A and 2B, for example, a right atrium lead, a right ventricle lead and a left ventricle lead can be used to perform CRT functions, and the left ventricle lead can further include a neural stimulator, such as an electrode placed in or near the coronary sinus or epicardially placed near a fat pad.

Figure 3:
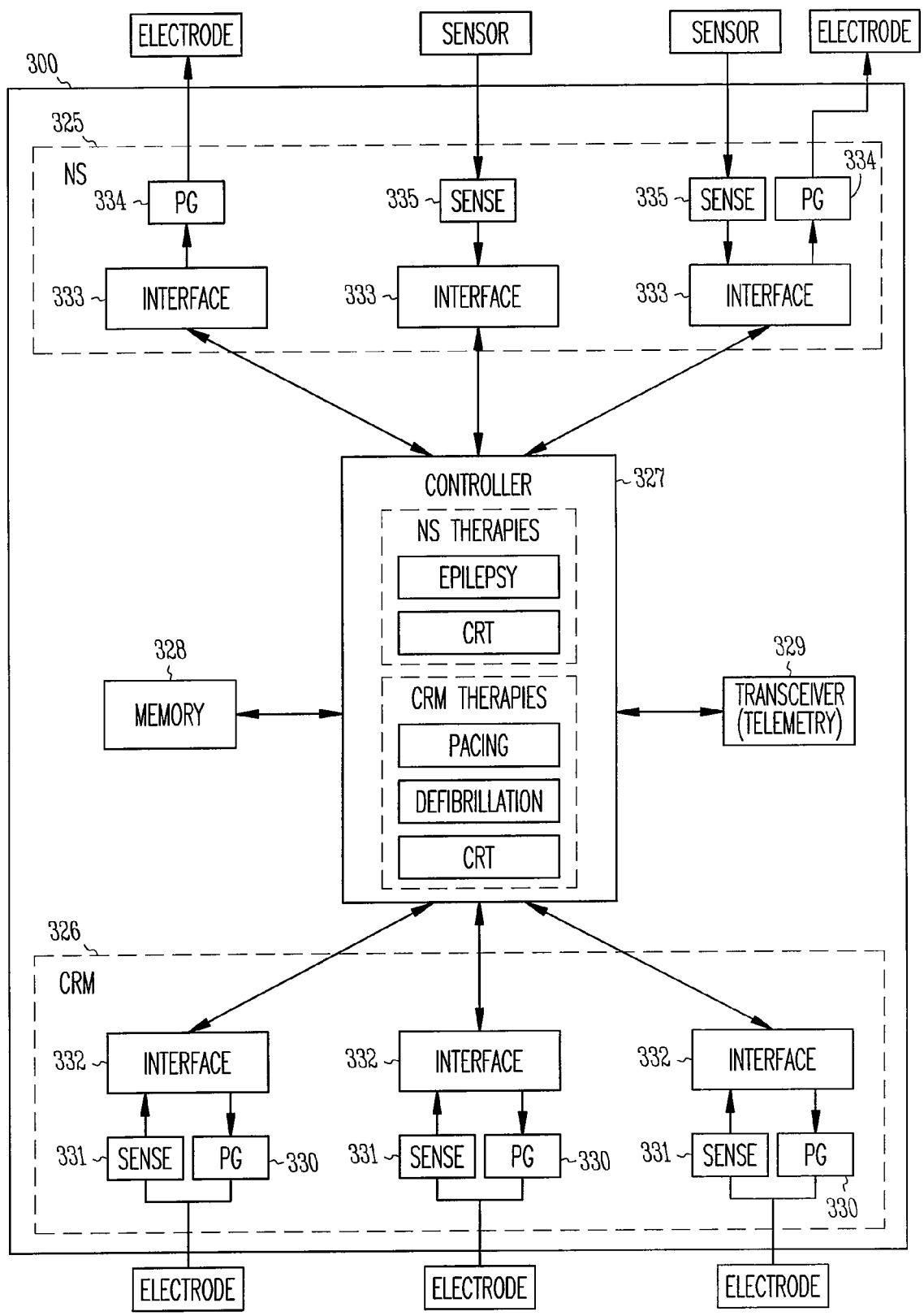
FIG. 3 illustrates an implantable medical device (IMD) 300 such as shown in FIG. 1 having a neural stimulation (NS) component and cardiac rhythm management (CRM) component, according to various embodiments of the present subject matter.

FIG. 3 illustrates an implantable medical device (IMD) 300 such as shown at 100 in FIG. 1 having a neural stimulation (NS) component 325 and cardiac rhythm management (CRM) component 326, according to various embodiments of the present subject matter. The illustrated device includes a controller 327 and a memory 328. According to various embodiments, the controller includes hardware, software, or a combination of hardware and software to perform the neural stimulation and CRM functions. For example, the programmed therapy applications discussed in this disclosure are capable of being stored as computer-readable instructions embodied in memory and executed by a processor. According to various embodiments, the controller includes a processor to execute instructions embedded in memory to perform the neural stimulation and CRM functions. As illustrated, the controller is adapted to provide neural stimulation to provide epilepsy therapy and CRT (ART). The illustrated controller also is adapted to provide myocardial stimulation to provide pacing, defibrillation and CRT (RCT). The illustrated device further includes a transceiver 329 and associated circuitry for use to communicate with a programmer or another external or internal device. Various embodiments include a telemetry coil.

The CRM therapy section 326 includes components, under the control of the controller, to stimulate a heart and/or sense cardiac signals using one or more electrodes. The CRM therapy section includes a pulse generator 330 for use to provide an electrical signal through an electrode to stimulate a heart, and further includes sense circuitry 331 to detect and process sensed cardiac signals. An interface 332 is generally illustrated for use to communicate between the controller 327 and the pulse generator 330 and sense circuitry 331. Three electrodes are illustrated as an example for use to provide CRM therapy. However, the present subject matter is not limited to a particular number of electrode sites. Each electrode may include its own pulse generator and sense circuitry. However, the present subject matter is not so limited. The pulse generating and sensing functions can be multiplexed to function with multiple electrodes.

The NS therapy section 325 includes components, under the control of the controller, to stimulate a neural stimulation target and/or sense ANS parameters associated with nerve activity or surrogates of ANS parameters such as blood pressure and respiration. Three interfaces 333 are illustrated for use to provide ANS therapy. However, the present subject matter is not limited to a particular number interfaces, or to any particular stimulating or sensing functions. Pulse generators 334 are used to provide electrical pulses to an electrode for use to stimulate a neural stimulation target. According to various embodiments, the pulse generator includes circuitry to set, and in some embodiments change, the amplitude of the stimulation pulse, the frequency of the stimulation pulse, the burst frequency of the pulse, and the morphology of the pulse such as a square wave, triangle wave, sinusoidal wave, and waves with desired harmonic components to mimic white noise or other signals. Sense circuits 335 are used to detect and process signals from a sensor, such as a sensor of nerve activity, blood pressure, respiration, and the like. The interfaces 333 are generally illustrated for use to communicate between the controller 327 and the pulse generator 334 and sense circuitry 335. Each interface, for example, may be used to control a separate lead. Various embodiments of the NS therapy section only include a pulse generator to stimulate neural targets such a vagus nerve for epilepsy therapy. The pulse generator is adapted to produce and deliver the stimulation signal with appropriate parameters effective for epilepsy therapy.

According to various embodiments, the lead(s) and the electrode(s) on the leads are physically arranged with respect to the heart in a fashion that enables the electrodes to properly transmit pulses and sense signals from the heart, and with respect to neural targets to stimulate, and in some embodiments sense neural traffic from, the neural targets. Examples of neural targets include both efferent and afferent pathways, such as nerve trunks and branches such as the vagus nerve (for use in epilepsy therapy, for example), and its cardiac branches, and such as cardiac fat pads and baroreceptors to provide a desired neural stimulation therapy. As there may be a number of leads and a number of electrodes per lead, the configuration can be programmed to use a particular electrode or electrodes.

The leads of the device include one or more leads to provide CRM therapy, such as atrial pacing, right and/or left ventricular pacing, antitachycardia pacing, defibrillation shocks, and/or CRT. Examples of neural stimulation leads include: an expandable stimulation lead placed in the pulmonary artery in proximity of a high concentration of baroreceptors; an intravascularly-fed lead placed proximate to a cardiac fat pad to transvascularly stimulate the fat pad; an epicardial lead with an electrode placed in or proximate to the fat pad; a cuff electrode placed around the aortic, carotid, or vagus nerve; and an intravascularly-fed lead placed to transvascularly stimulate the aortic, carotid or vagus nerve. According to the present subject matter, the vagus nerve is stimulated to provide epilepsy therapy. Other lead placements to stimulate other neural targets may be used for ART or for other neural stimulation therapies.

Figure 4:
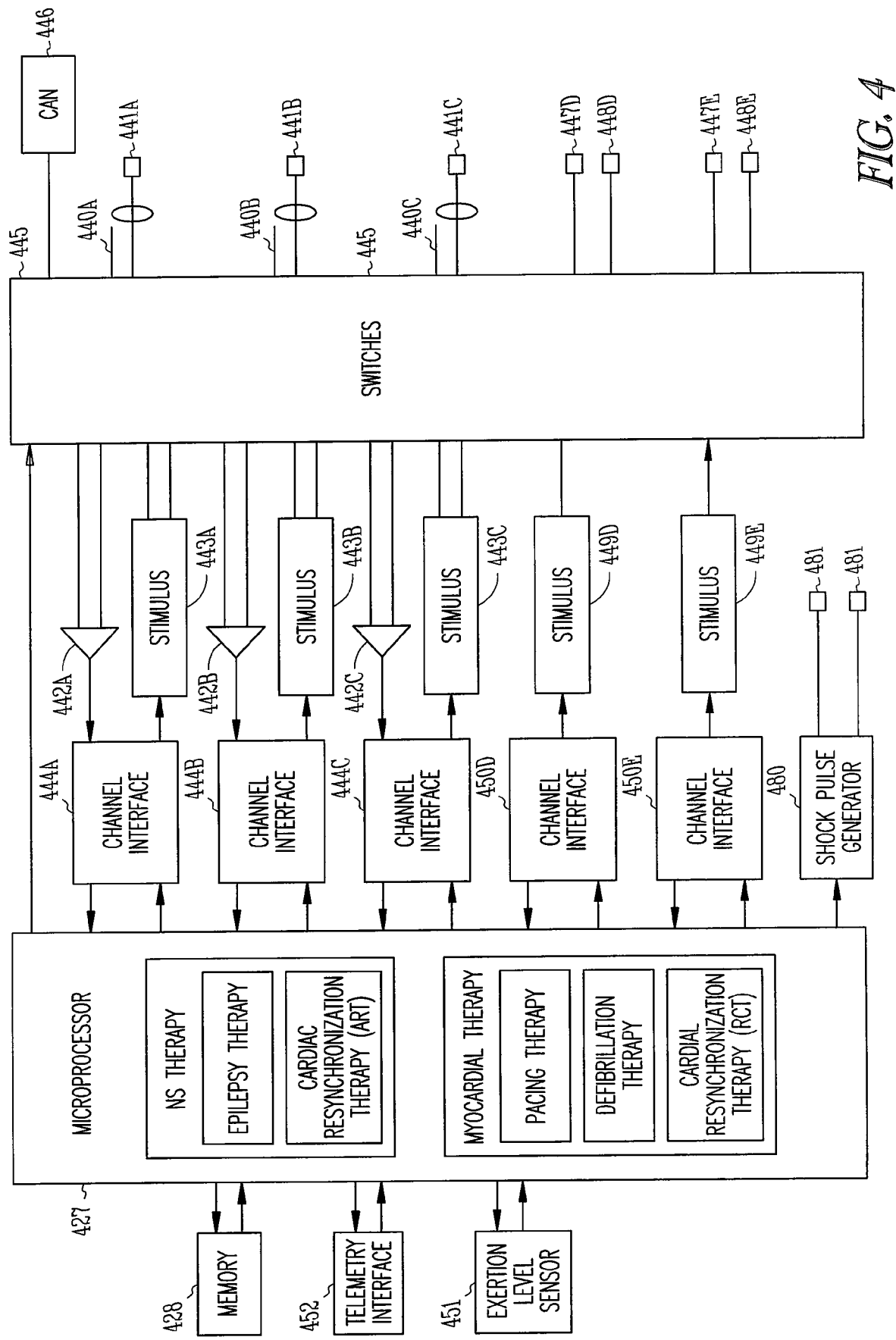
FIG. 4 shows a system diagram of an embodiment of a microprocessor-based implantable device.

FIG. 4 shows a system diagram of an embodiment of a microprocessor-based implantable device. The device is equipped with multiple sensing and pacing channels which may be physically configured to sense and/or pace multiple sites in the atria or the ventricles, and to provide neural stimulation. The illustrated device can be configured for myocardial stimulation (pacing, defibrillation, CRT/RCT) and neural stimulation (epilepsy therapy, CRT/ART). The multiple sensing/pacing channels may be configured, for example, with one atrial and two ventricular sensing/pacing channels for delivering biventricular resynchronization therapy, with the atrial sensing/pacing channel used to deliver the biventricular resynchronization therapy in an atrial tracking mode as well as to pace the atria if required. The controller 427 of the device is a microprocessor which communicates with a memory 428 via a bidirectional data bus. The controller could be implemented by other types of logic circuitry (e.g., discrete components or programmable logic arrays) using a state machine type of design, but a microprocessor-based system is preferable. As used herein, the term "circuitry" should be taken to refer to either discrete logic circuitry or to the programming of a microprocessor.

Shown in FIG. 4, by way of example, are three sensing and pacing channels, such as can be used to provide myocardial stimulation/pacing, designated "A" through "C" comprising bipolar leads with ring electrodes 440A-C and tip electrodes 441A-C, sensing amplifiers 442A-C, pulse generators 443A-C, and channel interfaces 444A-C. Each channel thus includes a pacing channel made up of the pulse generator connected to the electrode and a sensing channel made up of the sense amplifier connected to the electrode. The channel interfaces 444A-C communicate bidirectionally with microprocessor, and each interface may include analog-to-digital converters for digitizing sensing signal inputs from the sensing amplifiers and registers that can be written to by the microprocessor in order to output pacing pulses, change the pacing pulse amplitude, and adjust the gain and threshold values for the sensing amplifiers. The sensing circuitry of the pacemaker detects a chamber sense, either an atrial sense or ventricular sense, when an electrogram signal (i.e., a voltage sensed by an electrode representing cardiac electrical activity) generated by a particular channel exceeds a specified detection threshold. Pacing algorithms used in particular pacing modes employ such senses to trigger or inhibit pacing, and the intrinsic atrial and/or ventricular rates can be detected by measuring the time intervals between atrial and ventricular senses, respectively.

The electrodes of each bipolar lead are connected via conductors within the lead to a switching network 445 controlled by the microprocessor. The switching network is used to switch the electrodes to the input of a sense amplifier in order to detect intrinsic cardiac activity and to the output of a pulse generator in order to deliver a pacing pulse. The switching network also enables the device to sense or pace either in a bipolar mode using both the ring and tip electrodes of a lead or in a unipolar mode using only one of the electrodes of the lead with the device housing or can 446 serving as a ground electrode.

Also shown in FIG. 4, by way of example, are nerve stimulation channels designated "D" and "E." Neural stimulation channels are incorporated into the device. These channels can be used to deliver stimulation to a vagus nerve as part of an epilepsy therapy, and to parasympathetic stimulation and/or sympathetic inhibition for ART as part of a cardiac resynchronization therapy. The illustrated channels include leads with electrodes 447D and 448D and electrodes 447E and 448E, a pulse generator 449D and 449E, and a channel interface 450D and 450E. The illustrated bipolar arrangement is intended as a non-exclusive example. Other neural stimulation electrode arrangements are within the scope of the present subject matter. Other embodiments may use unipolar leads in which case the neural stimulation pulses are referenced to the can or another electrode. The pulse generator for each channel outputs a train of neural stimulation pulses which may be varied by the controller as to amplitude, frequency, duty-cycle, pulse duration, and wave morphology.

A shock pulse generator 480 is also interfaced to the controller for delivering a defibrillation shock via a pair of shock electrodes 481 to the atria or ventricles upon detection of a shockable tachyarrhythmia.

The illustrated controller includes a module for controlling neural stimulation (NS) therapy and module for controlling myocardial therapy. As illustrated, the NS therapy module includes a module for controlling epilepsy therapy by controlling the vagal stimulation. Also as illustrated, the myocardial therapy module includes a module for controlling pacing therapies, and a module for controlling defibrillation therapies. The illustrated controller is also adapted to control cardiac resynchronization therapy (CRT) by controlling RCT (a myocardial stimulation therapy), and in some embodiments by controlling ART (a neural stimulation therapy).

The controller controls the overall operation of the device in accordance with programmed instructions stored in memory, including controlling the delivery of paces via the pacing channels, interpreting sense signals received from the sensing channels, and implementing timers for defining escape intervals and sensory refractory periods. The controller is capable of operating the device in a number of programmed pacing modes which define how pulses are output in response to sensed events and expiration of time intervals. Most pacemakers for treating bradycardia are programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity such that a pacing pulse is delivered to a heart chamber during a cardiac cycle only after expiration of a defined escape interval during which no intrinsic beat by the chamber is detected. Escape intervals for ventricular pacing can be restarted by ventricular or atrial events, the latter allowing the pacing to track intrinsic atrial beats. CRT is most conveniently delivered in conjunction with a bradycardia pacing mode where, for example, multiple excitatory stimulation pulses are delivered to multiple sites during a cardiac cycle in order to both pace the heart in accordance with a bradycardia mode and provide pre-excitation of selected sites. An exertion level sensor 451 (e.g., an accelerometer, a minute ventilation sensor, or other sensor that measures a parameter related to metabolic demand) enables the controller to adapt the pacing rate in accordance with changes in the patient's physical activity and, as explained below, can enable the controller to modulate the delivery of neural stimulation and/or cardiac resynchronization pacing. A telemetry interface 452 is also provided which enables the controller to communicate with an external programmer or remote monitor.

Some embodiments of the present subject matter use the same hardware platform to provide both neural stimulation and myocardial stimulation, as provided in the following patent application: "System to Provide Myocardial and Neural Stimulation," Ser. No. 11/087,935, filed Mar. 23, 2005.

Figure 5:
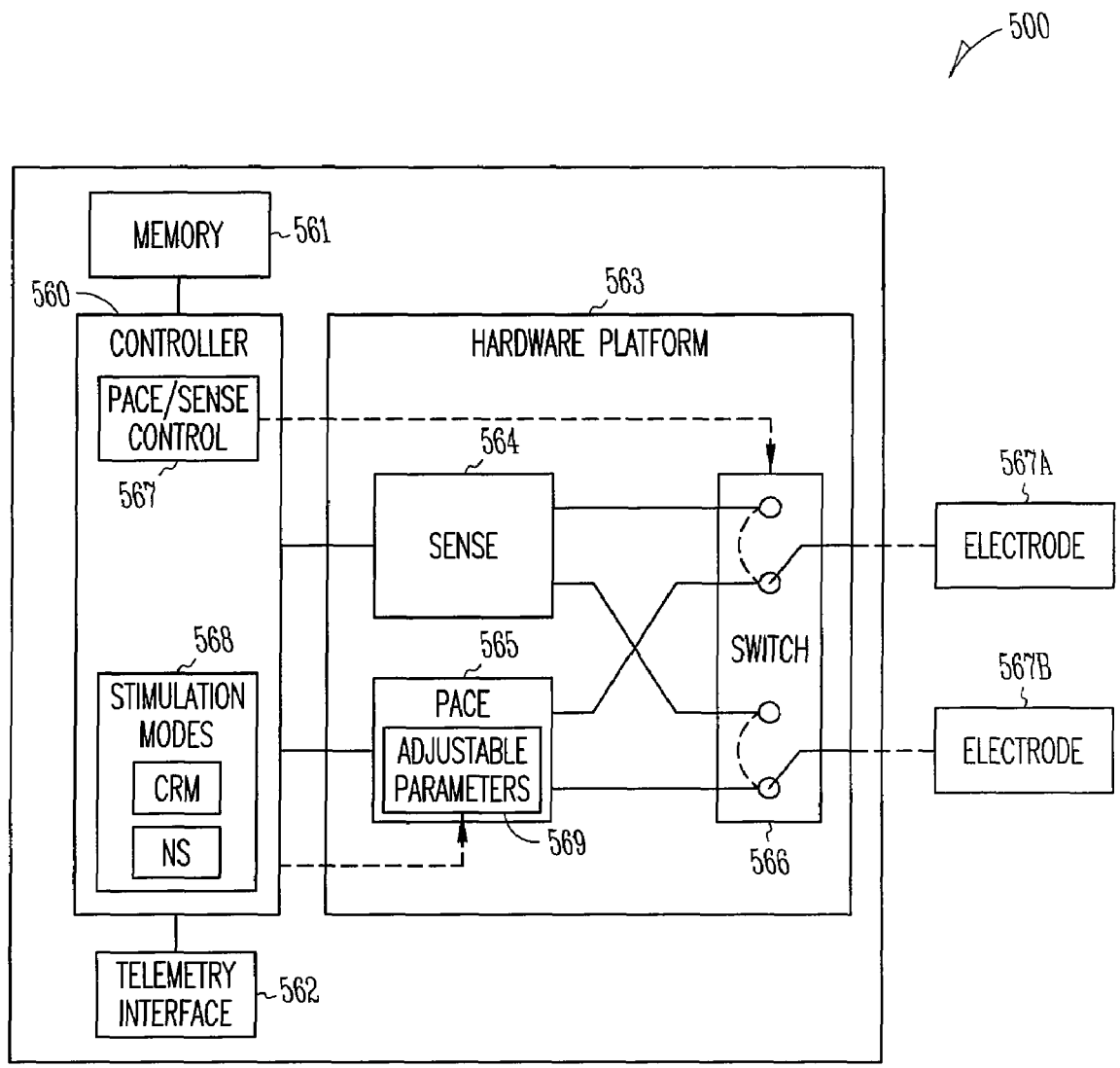
FIG. 5 illustrates an embodiment of an implantable medical device which uses the same hardware platform for both neural stimulation and myocardial stimulation.

FIG. 5 illustrates an embodiment of an implantable medical device 500 which uses the same hardware platform for both neural stimulation and myocardial stimulation. The illustrated device includes a controller 560 to communicate with a memory 561, a telemetry interface 562 for use in communicating with a programmer (not illustrated) of the implantable medical device, and a stimulating/sensing hardware platform 563. The illustrated hardware platform includes a sense module 564, a pace module 565, and switches 566 for use to operably connect the sense module and the pace module to the electrodes 567A and 567B. The illustrated electrodes can be two electrodes on one lead, such as a tip and ring electrode or can be on separate leads. Additionally, one of the electrodes can be a conductive portion, also referred to as a "can", of the implantable medical device. The illustrated controller includes a pace/sense control module 567 to control the switches and selectively enable the sense module to operably connect to the electrodes and sense a potential across the electrodes or the pace module to operably connect to the electrodes and apply a pacing signal to generate a pacing potential between the electrodes to provide a desired electrical stimulus to a patient.

The illustrated controller includes a stimulation mode module 568, and the illustrated pace module includes adjustable parameters 569, such as, for example, amplitude, frequency, waveform, and pacing mode. The parameters of the pace module are able to be adjusted to selectively provide a neural stimulation signal to the electrodes or a myocardial stimulation signal to the electrodes. In some embodiments, the parameters are able to be adjusted to selectively apply a neural stimulation signal adapted to simultaneously provide myocardial and neural stimulation. According to various embodiments, the stimulation mode module is adapted to selectively apply CRM or myocardial stimulation using the electrodes, neural stimulation using the electrodes, selectively alternate between myocardial and neural stimulation using the electrodes according to a desired therapy, and/or simultaneously apply both myocardial and neural stimulation using the electrodes. The illustrated pace module includes adjustable parameters.

Figure 6:
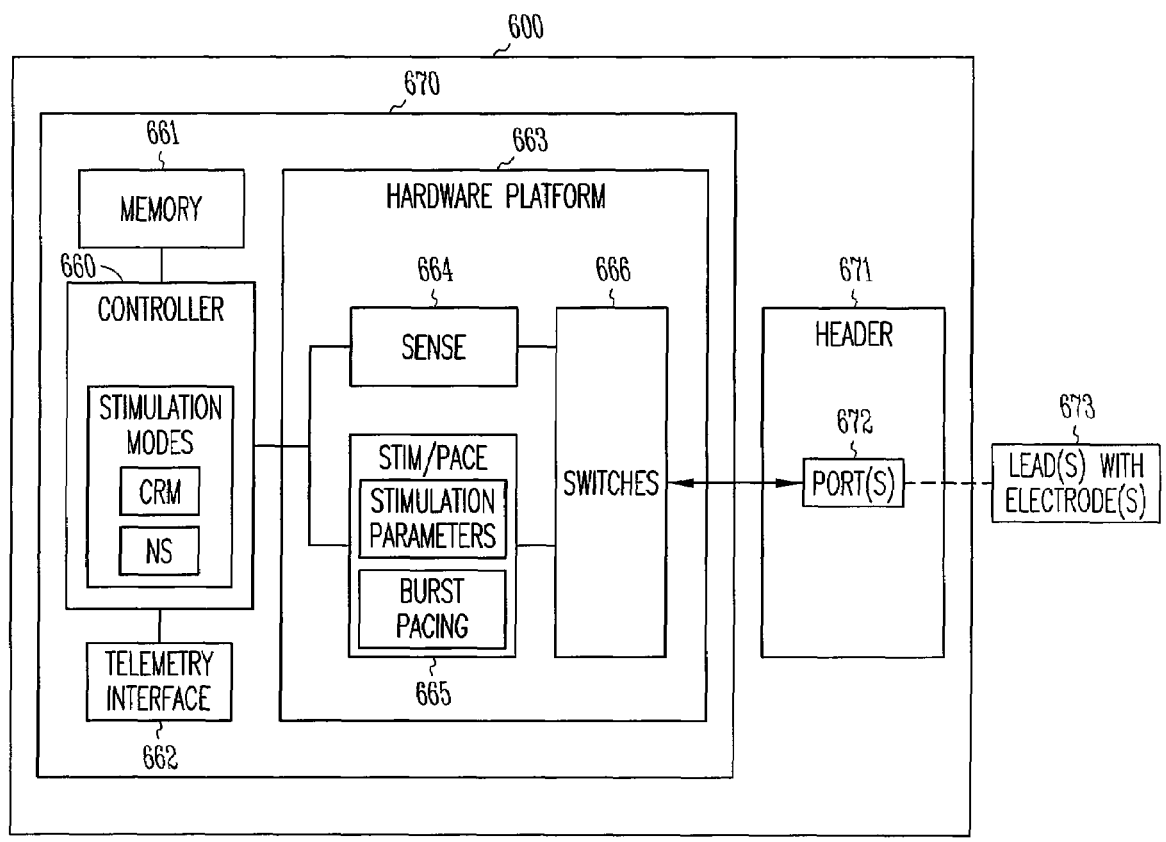
FIG. 6 illustrates a multi-channel embodiment of an implantable medical device.

FIG. 6 illustrates a multi-channel embodiment of an implantable medical device. The illustrated device 600 includes a pulse generator housing 670, and the pulse generator includes a controller 660 to communicate with a memory 661, a telemetry interface 662 for use in communicating with a programmer of the implantable medical device, and a hardware platform 663. The illustrated hardware platform includes a sense module 664, a stimulation or pace module 665, and switches 666 for use to operably connect the sense module and the pace module to a header 671. The header includes one or more ports 672 to receive a lead 673, for example. Each lead can include one or more electrodes. Rather than using leads, wireless links can be used to connect to the electrodes to provide the electrical stimulation, and in some embodiments, communicate sensed signals. The switches selectively provide desired connections between the sense and pace modules and the ports in the header to provide desired pace channels between the pace module and desired electrode(s) on the lead(s), and to provide desired sense channels between the sense module and desired electrode(s) on the lead(s). In various embodiments, the can of the implantable medical device is used as an electrode. Some embodiments of the pace module include circuitry to independently and simultaneously provide stimulation signals on multiple channels.

The controller includes a pace/sense control module to control the switches and selectively enable the sense module to operably connect to the electrodes and sense a potential across the electrodes or the pace module to operably connect to the electrodes and apply a pacing signal to generate a pacing potential between the electrodes to provide a desired electrical stimulus to a patient.

The illustrated controller includes a stimulation mode module, and the illustrated pace module includes adjustable stimulation parameters, including burst pacing parameters. The parameters of the pace module are able to be adjusted to selectively provide a neural stimulation signal to selected electrodes or a myocardial stimulation signal to selected electrodes. In some embodiments, the stimulation parameters of the pace module are able to be adjusted to selectively apply a neural stimulation signal adapted to simultaneously provide myocardial and neural stimulation. According to various embodiments, the stimulation mode module is adapted to selectively apply CRM or myocardial stimulation using the electrodes, neural stimulation using the electrodes, selectively alternate between myocardial and neural stimulation using the electrodes according to a desired therapy, and/or simultaneously apply both myocardial and neural stimulation using the electrodes.

One of ordinary skill in the art will understand that, the modules and other circuitry shown and described herein can be implemented using software, hardware, and combinations of software and hardware. As such, the illustrated modules and circuitry are intended to encompass software implementations, hardware implementations, and software and hardware implementations.

The methods illustrated in this disclosure are not intended to be exclusive of other methods within the scope of the present subject matter. Those of ordinary skill in the art will understand, upon reading and comprehending this disclosure, other methods within the scope of the present subject matter. The above-identified embodiments, and portions of the illustrated embodiments, are not necessarily mutually exclusive. These embodiments, or portions thereof, can be combined.

In various embodiments, the methods provided above are implemented as a computer data signal embodied in a carrier wave or propagated signal, that represents a sequence of instructions which, when executed by a processor cause the processor to perform the respective method. In various embodiments, methods provided above are implemented as a set of instructions contained on a computer-accessible medium capable of directing a processor to perform the respective method. In various embodiments, the medium is a magnetic medium, an electronic medium, or an optical medium.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments as well as combinations of portions of the above embodiments in other embodiments will be apparent to those of skill in the art upon reviewing the above description. The scope of the present subject matter should be determined with reference to the appended claims, along with the full scope of equivalents to which such claims are entitled.

What is claimed is:

1. An implantable device, comprising:
   at least one pulse generator adapted to deliver a first electrical signal through at least one electrode positioned proximate to a vagus nerve and to deliver a second electrical signal through at least one electrode positioned within or proximate to the heart; and
   a controller adapted to communicate with the at least one pulse generator, the controller including a module to provide epilepsy therapy that includes delivering the first electrical signal though the at least one electrode proximate to the vagus nerve and a module to provide a cardiac rhythm management (CRM) therapy that includes delivering the second electrical signal through at least one electrode positioned within or proximate to the heart, the CRM therapy including at least one therapy selected from an antitachycardia therapy and a cardiac resynchronization therapy (CRT), wherein the CRT is adapted to electrically stimulate myocardial tissue to coordinate contractions of contralateral cardiac chambers.

2. The device of claim 1, wherein the CRM therapy further includes a pacing therapy.

3. The device of claim 1, wherein the at least one therapy includes both the antitachycardia therapy and the CRT.

4. The device of claim 1, wherein the at least one therapy only includes the antitachycardia therapy.

5. The device of claim 1, wherein the antitachycardia therapy includes an antitachycardia pacing therapy.

6. The device of claim 1, wherein the antitachycardia therapy includes a defibrillation shock.

7. The device of claim 1, wherein the at least one electrode positioned proximate to a vagus nerve includes at least one electrode positioned proximate to a left vagus nerve.

8. The device of claim 1, wherein the at least one electrode positioned proximate to a vagus nerve includes at least one electrode positioned proximate to a right vagus nerve.

9. The device of claim 1, wherein the at least one electrode positioned proximate to a vagus nerve includes at least one electrode positioned proximate to a left vagus nerve and at least one electrode positioned proximate to a right vagus nerve.

10. The device of claim 1, wherein the at least one electrode positioned proximate to a vagus nerve includes a nerve cuff electrode adapted to stimulate the vagus nerve.

11. The device of claim 1, wherein the at least one electrode positioned proximate to a vagus nerve includes an intravascular electrode adapted to transvascularly stimulate the vagus nerve from a position within a vessel proximate to the vagus nerve.

12. The device of claim 11, wherein the vessel includes an internal jugular vein.

13. The device of claim 11, wherein the vessel includes an azygous vein.

14. The device of claim 1, wherein the CRT includes myocardial stimulation to provide remodeling control therapy (RCT).

15. The device of claim 14, wherein the CRT further includes neural stimulation to provide anti-remodeling therapy (ART).

16. An implantable device, comprising:
   at least one pulse generator adapted to deliver a first electrical signal through at least one electrode positioned proximate to a vagus nerve and to deliver a second electrical signal through at least one electrode positioned within or proximate to the heart; and
   a controller adapted to communicate with the at least one pulse generator, the controller including a module to provide epilepsy therapy that includes delivering the first electrical signal though the at least one electrode proximate to the vagus nerve and a module to provide a cardiac resynchronization therapy (CRT) that includes delivering the second electrical signal through at least one electrode positioned within or proximate to the heart, wherein the module to provide the CRT is adapted to control timing of electrical stimulation of myocardial tissue to coordinate contractions of contralateral cardiac chambers.

17. The device of claim 16, wherein the CRM therapy further includes at least one therapy selected from a pacing therapy and an antitachycardia therapy.

18. The device of claim 16, wherein the at least one electrode positioned proximate to a vagus nerve includes a nerve cuff electrode adapted to stimulate the vagus nerve.

19. The device of claim 16, wherein the at least one electrode positioned proximate to a vagus nerve includes an intravascular electrode adapted to transvascularly stimulate the vagus nerve from a position within a vessel proximate to the vagus nerve.

20. An implantable device, comprising:
means for providing epilepsy therapy, including means for applying electrical stimulation of a vagus nerve; and
means for providing at least one therapy selected from a cardiac antitachycardia therapy and a cardiac resynchronization therapy (CRT) adapted to electrically stimulate myocardial tissue with appropriate timing to coordinate contractions of contralateral cardiac chambers.

21. The device of claim 20, wherein the means for providing at least one therapy selected from a cardiac antitachycardia therapy and a cardiac resynchronization therapy (CRT) includes means for providing the CRT.

22. The device of claim 20, wherein the means for providing at least one therapy selected from a cardiac antitachycardia therapy and a cardiac resynchronization therapy (CRT) includes means for providing the cardiac antitachycardia therapy.

23. The device of claim 20, further comprising means for providing a pacing therapy.

24. The device of claim 20, further comprising means for simultaneously providing epilepsy therapy and the at least one therapy selected from the cardiac antitachycardia therapy and the CRT.

25. A method of operating an implantable device, comprising:
providing epilepsy therapy, including using the implantable device to deliver an electrical stimulation to a vagus nerve; and
providing a cardiac rhythm management (CRM) therapy, including at least one therapy selected from an antitachycardia therapy and a cardiac resynchronization therapy (CRT), wherein providing the CRM therapy includes using the implantable device to deliver an electrical stimulation to capture myocardial tissue, and the CRT therapy includes controlling the timing of the electrical stimulation to coordinate contractions of contralateral cardiac chambers.

26. The method of claim 25, wherein the at least one therapy includes the CRT.

27. The method of claim 25, wherein the at least one therapy includes the antitachycardia therapy.

28. The method of claim 25, further comprising providing a pacing therapy using the implantable medical device to deliver an electrical stimulation to capture myocardial tissue.

* * * * *

UNITED STATES PATENT AND TRADEMARK OFFICE
CERTIFICATE OF CORRECTION

| | | |
|---|---|---|
| PATENT NO. | : 7,570,999 B2 | Page 1 of 1 |
| APPLICATION NO. | : 11/312178 | |
| DATED | : August 4, 2009 | |
| INVENTOR(S) | : Libbus et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 444 days.

Signed and Sealed this

Seventh Day of September, 2010

David J. Kappos
*Director of the United States Patent and Trademark Office*